United States Patent [19]

Palmenberg et al.

[11] Patent Number: 5,229,111
[45] Date of Patent: Jul. 20, 1993

[54] METHOD OF INHIBITING PICORNAVIRUS DISEASE

[75] Inventors: Ann C. Palmenberg; Gregory M. Duke, both of Madison; Jorge E. Osorio, Oregon, all of Wis.

[73] Assignee: Wiscosnin Alumni Research Foundation, Madison, Wis.

[21] Appl. No.: 648,098

[22] Filed: Jan. 31, 1991

[51] Int. Cl.$^5$ .................. A61K 39/12; C12N 15/00
[52] U.S. Cl. ..................... 424/89; 435/172.3; 435/317.1; 435/320.1; 935/56; 935/57; 935/65
[58] Field of Search ............ 424/89; 435/172.3, 320.1, 435/317.1; 935/56, 57, 65

[56] References Cited

U.S. PATENT DOCUMENTS 4,743,554 5/1988 Boothroyd et al. ............... 435/172.3

OTHER PUBLICATIONS

Osorio, J. et al., "Attenuation of Mengovirus Pathogenicity Through Recombinant Engineering of the Poly(C) Tract," In American Society for *Virology 8th Annual Meeting*, Jul. 9–13, 1989 (Abstract).

Osorio J., et al., "Attenuation of Mengovirus Pathogenicity Through Recombinant Engineering of the Poly(C) Tract," in Europic 89, Sixth *Meeting of the European Study Group on the Molecular Biology of Picornaviruses*, Bruges, Belgium Sep. 10–16, 1989 (Abstract).

Duke, G. M. and A. C. Palmenberg, "Cloning and Synthesis of Infectious Cardiovirus RNAs Containing Short, Discrete Poly(C) Tracts," J. Virology 63[4] 1822–1826 (1989).

Duke, G. M. et al., "Attenuation of Mengovirus Through Genetic Engineering of the 5' Noncoding Poly(C) Tract," *Nature* 343[6257] 474–476 (Feb. 1, 1990).

Rueckert, R. R. and M. A. Pallansch, "Preparation and Characterization of Encephalomyocarditis (EMC) Virus," *Methods in Enzymology* 78: 315–325 (1981).

Oxford Veterinary Laboratories, Inc. advertisement, "EMC virus has been isolated," 1990.

Quaife, T., "Helping Labs to Solve a 'Mystery' Disease," *Swine Practitioner* 8–13 (Feb., 1990).

Gainer, J. H., "Encephalomyocarditis Virus Infections in Florida, 1960–1966," *J.A.V.M.A.*, 151[4]: 421–425 (1967).

Joo, H. S., et al., "Detection of Antibody to Encephalomyocarditis Virus in Mummified or Stillborn Pigs," *Arch. Virol.* 100: 131–134 (1988).

Maes et al, *Biological Abstracts*, 6975 (Dec. 15, 1978), Reference No. 70853 (Arch. Virol. 55(4):275–286, 1977).

Stebbing et al, *Infection and Immunity*, vol. 29, No. 3, pp. 960–965, Sep. 1980.

Andzhaporidze et al, *Biological Abstract*, 1925 (Aug. 15, 1978). Reference No. 19678 (VOPR Virusol (3):339–343, 1977).

*Primary Examiner*—Jeffrey E. Russel
*Assistant Examiner*—Abdel A. Mohamed
*Attorney, Agent, or Firm*—Quarles & Brady

[57] ABSTRACT

A method for inhibiting picornavirus disease in non-murine mammals is disclosed. A vaccine containing a live, recombinant, attenuated picornavirus with a shortened poly(C) tract is administered to the mammal. Preferably, the picornavirus in the vaccine is of the same genus as the disease-causing picornavirus and has a shortened poly(C) tract. The administration of the vaccine causes antibodies effective against the disease-causing picornavirus to be formed in vivo. In one embodiment of the invention, a vaccine containing Mengovirus with a shortened poly(C) tract can be used as a vaccine for both pigs and monkeys.

9 Claims, 5 Drawing Sheets

FIG. 2

IM INOCULATION 8 LOG (pfu) pM16 VIRUS

| DAY | ANIMAL 40<br>Ab (LOG(N)) | ANIMAL 41<br>Ab (LOG(N)) |
|---|---|---|
| 0 | 0.30 | 0.30 |
| 2 | 0.60 | 0.60 |
| 4 | 3.01 | 3.01 |
| 7 | 3.31 | 3.01 |
| 14 | 3.91 | 3.91 |
| 21 | 4.21 | 3.91 |
| 100 | 3.91 | 3.61 |

ORAL INOCULATION OF 8 LOG (pfu) OF pM16 VIRUS

| DAY | ANIMAL 42<br>Ab (LOG(N)) | ANIMAL 43<br>Ab (LOG(N)) |
|---|---|---|
| 0 | 0.30 | 0.30 |
| 2 | 0.30 | 0.30 |
| 4 | 0.30 | 0.30 |
| 7 | 0.60 | 0.60 |
| 14 | 3.61 | 3.31 |
| 21 | 3.91 | 3.91 |
| 100 | 3.61 | 3.61 |

| (LOG (pfu)) DOSE | ANIMAL | SAMPLE | DAY - 0 | DAY - 2 | DAY - 4 | DAY - 9 | DAY - 22 |
|---|---|---|---|---|---|---|---|
| 3 | 53 | SERUM Ab TITRE | <4 | <4 | <4 | >512 | 3992 |
| 3 | 61 | SERUM Ab TITRE | <4 | <4 | 6 | >512 | <4049 |
| 4 | 60 | SERUM Ab TITRE | <4 | <4 | <4 | 16 | 14943 |
| 4 | 64 | SERUM Ab TITRE | <4 | <4 | 579 | 36633 | 23643 |
| 5 | 51 | SERUM Ab TITRE | <4 | <4 | 145 | >4096 | 17362 |
| 5 | 58 | SERUM Ab TITRE | <4 | <4 | 127 | 10594 | >32768 |
| 6 | 48 | SERUM Ab TITRE | <4 | <4 | 722 | 9554 | 16299 |
| 6 | 57 | SERUM Ab TITRE | <4 | <4 | >512 | 12719 | 25376 |
| 7 | 52 | SERUM Ab TITRE | <4 | <4 | >512 | 6798 | 13206 |
| 7 | 59 | SERUM Ab TITRE | <4 | <4 | >512 | 11997 | NT |

FIG. 3

Bilateral Intrathalamic Inoculation of 2x8 log (pfu) of pM16 virus.

| ANIMAL | SAMPLE | DAY = 0 | DAY = 3 | DAY = 5 | DAY = 7 | DAY = 10 | DAY = 14 |
|---|---|---|---|---|---|---|---|
| 46 | SERUM Ab LEVEL | <4 | 8 | DIED | | | |
| 63 | SERUM Ab LEVEL | <4 | 61 | 1270 | 3034 | 6087 | 13280 |
| 65 | SERUM Ab LEVEL | <4 | 80 | 2979 | 2789 | 4459 | 9991 |

FIG. 4

| ANIMAL | SAMPLE | DAY=0 | DAY=7 | DAY=15 | DAY=21 | DAY=28 | DAY=42 |
|---|---|---|---|---|---|---|---|
| 1 | SERUM | <2 | 64 | 1028 | 512 | 512 | |
| 2 | SERUM | <2 | <2 | 16 | 64 | 64 | |
| 3 | SERUM | <2 | 8 | 512 | 512 | 256 | 512 |
| 4 | SERUM | <2 | <2 | <2 | <2 | <2 | |
| 5 CNTL | SERUM | <2 | <2 | <2 | <2 | <2 | |
| 6 CNTL | SERUM | <2 | <2 | <2 | <2 | <2 | |

FIG. 5

METHOD OF INHIBITING PICORNAVIRUS DISEASE

This invention was made with U.S. government support awarded by the National Institute of Health (NIH), Grant #AI-17331. The U.S. Government has certain rights in this invention.

The present invention relates to a vaccine against picornaviral disease. More particularly, it relates to a vaccine against picornaviral disease that contains a recombinant, attenuated picornavirus.

BACKGROUND OF THE INVENTION

Picornaviruses are positive-strand RNA viruses that contain a long open-reading-frame encoding a polyprotein. Cardioviruses and aphthoviruses are two genera of picornaviruses. The 5'-end non-coding sequences for these genera are typically 750 to 1,300 nucleotides in length. Some strains of cardioviruses and aphthoviruses have a homopolymeric non-coding poly(C) tract which is located about 150 to 330 bases from the 5'-end of the RNA strand.

The length of the poly(C) tract in cardioviruses and aphthoviruses is usually between 60 to 200 bases and the tract may include discontinuities, such as the insertion of a U residue within the stretch of poly(C). With respect to wild-type virus, by poly(C) tract, we mean any stretch of residues longer than 20 residues which is at least 75% C, ends and begins with a sequence of at least four consecutive C residues, and is within the 5' noncoding region of a wild-type picornavirus genome. Our convention is to count the discontinuities within the tract when we refer to the length of the tract. For example, a tract of $C_{13}UC_{10}$ is a tract of 24 residues.

Both the length of the poly(C) tract and the particular discontinuities are characteristics of a particular strain of cardiovirus or aphthovirus. Examples of poly(C) tractcontaining cardioviruses are Mengoviruses, EMCV (encephalomyocarditis virus), ME (Maus Elberfeld), Columbia SK, and MM. Foot and mouth disease virus (FMDV) is an example of an aphthovirus containing a poly(C) tract.

Mengovirus and EMCV had been considered primarily murine (rodent) in their host range. However, isolated reports of cardiovirus infections in non-murine mammals (e.g., humans, non-human primates, swine, elephants, and lions) have been published. Very recently, improved serotypic detection methods have demonstrated the extent and prevalence of cardiovirus-induced infections among animals. For example, the "mystery disease" affecting pig herds in Indiana, Iowa, Minnesota and other states is now attributed to EMCV. Joo, et al., *Arch. Virol.* 100: 131-134 (1989). (The disclosures of all articles recited herein are incorporated by reference as if fully set forth below.) Recently, some captive primate colonies, such as domestic breeding facilities and zoos, have reported loss of animals because of EMCV infections. The clinical signs of EMCV infection are high rate of stillbirth, fever, lack of appetite, and late-term abortions. Baby pigs affected with EMCV are weak and have labored breathing. Autopsies of infected animals have revealed enlarged hearts with white striations or spots.

The host range of FMDV is primarily bovine. FMDV infection is believed to cause a significant loss of cattle in European and certain other countries.

There is therefore a great need for vaccines against disease caused by EMCV, FMDV, and other picornaviruses. Certain currently available vaccines, such as an EMCV vaccine from Oxford Veterinary Laboratories, Inc. (Worthington, Minn.), are "killed virus" vaccines. A killed virus vaccine contains a wild-type virus that has been inactivated, usually through chemical means. These vaccines have the disadvantage of shorter duration of immunity than an attenuated live virus vaccine. (An "attenuated" virus is a live virus that has a lessened capability to cause disease when compared to the wild-type virus.)

Recent inoculation studies in our laboratory with mice have demonstrated that a genetically engineered Mengovirus containing an artificially shortened poly(C) tract was attenuated compared to wild-type viruses. Osorio, et al. "Attenuation of Mengovirus Pathogenicity through Recombinant Engineering of the Poly(C) Tract," in *Europic 89, Sixth Meeting of the European Study Group on the Molecular Biology of Picornaviruses*, Bruges, Belgium, Sep. 10-16, 1989 (Abstract).

Although use of short poly(C) tract Mengovirus has been reported with respect to mice, picornavirus vaccines effective in pigs, monkeys and other animals are still needed. Living things are classified according to the following scheme: Kingdom, Phylum, Class, Order, Family, Genus, and Species. While all mammals belong to the same class, primates (e.g. monkeys and humans), rodents, and pigs each belong to different orders. Prior to our invention, there were no known attenuated vaccines that were reactive across different taxonomic orders.

SUMMARY OF THE INVENTION

One aspect of the present invention is a method of inhibiting disease caused by a picornavirus in a live, non-murine mammal. The disease-causing picornavirus is of a type that contains a non-coding poly(C) tract of at least 50 residues. An effective amount of a vaccine containing a recombinant picornavirus that has a shortened poly(C) tract is administered to the mammal. Antibodies effective against the disease-causing picornavirus are formed in vivo in the mammal.

In a preferred form of the invention, the disease-causing picornavirus and the picornavirus contained within the vaccine are of the same genus.

Another aspect of the present invention is a method of inhibiting disease caused by a cardiovirus in a live, non-murine mammal. The disease-causing cardiovirus is of a type that contains a non-coding poly(C) tract of at least 50 residues. An effective amount of a vaccine containing a recombinant cardiovirus that has a shortened poly(C) tract is administered to the mammal. Antibodies effective against the disease-causing cardiovirus are formed in vivo in the mammal.

In a preferred form of the invention the mammal to be protected is a member of the primate or Artiodactyla (hoofed animals, such as pigs) orders.

In an especially preferred form of the invention, the picornavirus contained within the vaccine is a Mengovirus and has a shortened poly(C) tract of less than 40 residues.

An object of the present invention is to protect non-murine mammals from picornaviral infection.

Another object of the invention is to use a single virus as a vaccine which is effective for mammals in more than one order.

Another object of the invention is to protect non-murine mammals from cardioviral disease.

These and other objects and advantages will be apparent from the description of the preferred embodiment.

DESCRIPTION OF THE FIGURES

FIG. 2 is a chart comparing intramuscular and oral routes of inoculation of pM16 mengovirus vaccine in primates;

FIG. 3 is a chart comparing the effect of increasing intramuscular doses of pM16 Mengovirus vaccine in primates;

FIG. 4 is a chart comparing the intracerebral inoculation of Mengovirus vaccine in primates; and FIG. 5 is a chart comparing the effects of intramuscular inoculation of six members of the order Artiodactyla.

DESCRIPTION OF THE PREFERRED EMBODIMENTS

Figure 1:
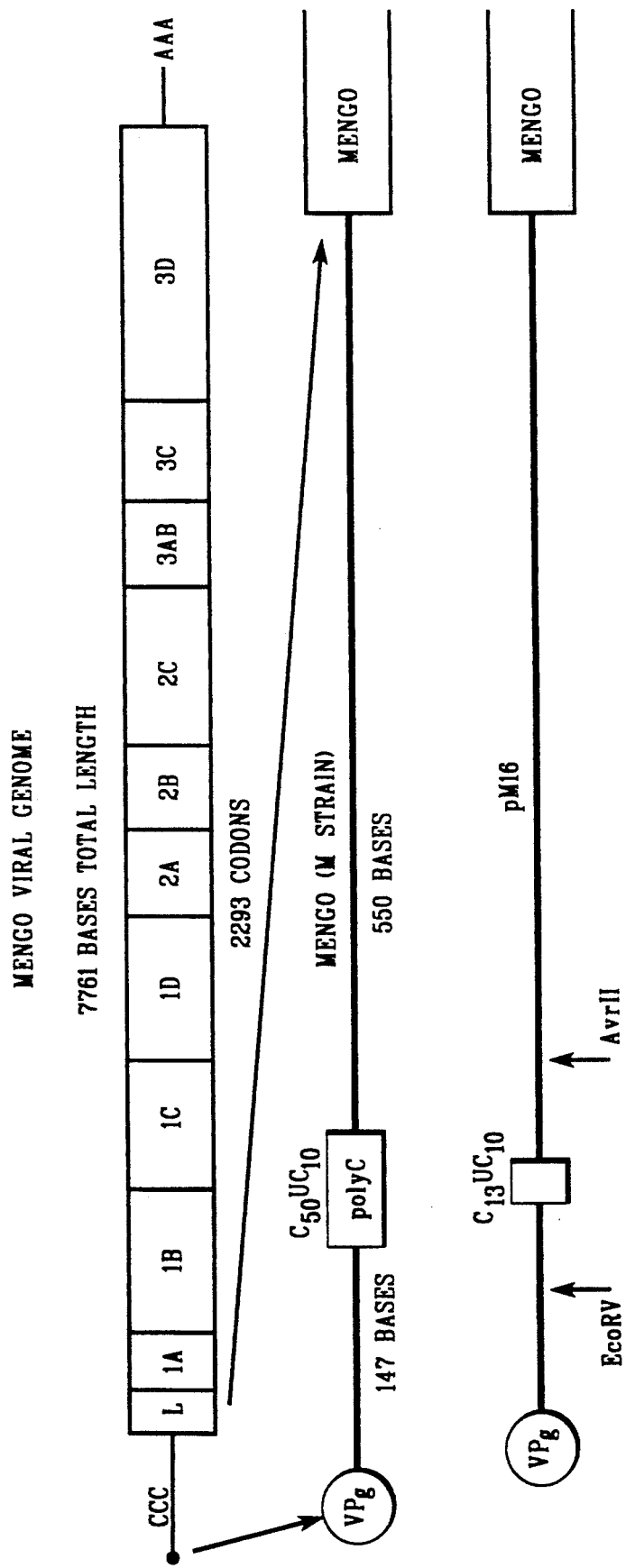
FIG. 1 is a schematic depiction of the wild-type Mengovirus with a comparison to the pM16 vaccine.

The descriptions of the preferred embodiments below are examples of the invention. They are not intended to represent the full scope of the invention. Therefore, the claims should be examined to determine the full scope of the invention.

Duke and Palmenberg, *J. Virology* 63[4] 1822-1826 (1989), describes the construction Mengovirus RNA transcripts with 5'-noncoding poly(C) tracts of $C_8$, $C_{12}$, and $C_{13}UC_{10}$. FIG. 1 of this patent describes the wild-type Mengovirus and its progeny clone, pM16. For convenience, we have developed a numbering convention to describe the Mengovirus RNA genome. The numbering convention starts at the 5'-end of the Mengovirus RNA molecule. Bases 148-208 of the wild-type virus are the poly(C) tract and its discontinuities. Bases 759-7637 are the polyprotein coding region.

Mengovirus RNA was isolated using the method of Rueckert and Pallansch, *Methods in Enzymology*, 78: 315-325 (1981). First-strand cDNA was synthesized using Mengovirus RNA (vRNA), oligo ($dT_{12}$) and avian myeloblastosis virus reverse transcriptase. Second-strand cDNA was synthesized in a replacement reaction by using the annealed vRNA as the primer. BamHI linkers were added, and the double-stranded cDNA was ligated into a pUC9 vector. This construction was used to transform JM101 cells to ampicillin resistance. The ampicillin resistant transformants were screened for the BamH1 insert. The largest insert was a nearly full length copy of Mengovirus RNA that contained viral base 21 to the poly(A) stretch.

The remaining 5'-end fragment was obtained by using a synthetic oligodeoxynucleotide complementary to vRNA bases 360-371. This oligodeoxynucleotide was used to prime cDNA synthesis on the vRNA with reverse transcriptase. Second-strand cDNA was synthesized in a replacement reaction using oligo ($dC_{12-18}$) as a primer after the addition of 10 to 20 dG residues on the 3'-end of the cDNA. The resulting double-stranded cDNA was ligated into M13mp19.

The M13mp19/cDNA construct was used to transform JM101 cells. The single-stranded DNA from the resulting plaques was sequenced by dideoxy sequencing methods. One clone contained an insert with 14 dG residues followed by bases 1-142 from the Mengovirus genome. By using a unique EcoRV restriction endonuclease site within the Mengovirus cDNA sequence, bases 1-45 from this second clone were joined to base 46 through the poly(A) tract from the first clone. FIG. 1 depicts the location of this EcoRV site. The resulting cDNA fragment was placed between the EcoRI and BamH1 sites of Bluescribe M13+ (Stratagene). The plasmid that resulted was designated pM16. Virus produced by pM16 was deposited with the American Type Culture Collection, Rockville, Md., U.S.A. with Accession Number VR2310 on Jan. 30, 1991. The deposit will be made available as required by applicable patent law. Such availability is not to be construed as a license under any patent.

Sequence analysis of the Mengovirus 5'-end non-coding region of pM16 DNA showed that it contained a much shorter poly(C) tract than wild-type Mengovirus. The natural sequences that flank the poly(C) tract were present in pM16, but the poly(C) tract itself was 37 bases shorter than that of the wild-type Mengovirus. Full-length Mengovirus has a poly(C) tract sequence of $C_{50}UC_{10}$. pM16 has the poly(C) tract sequence of $C_{13}UC_{10}$.

In the course of constructing pM16, other Mengovirus cDNA fragments were sequenced. Two isolates had poly(C) tracts of $C_8$ and $C_{12}$, respectively. The AvrII - EcoRV fragment of pM16 was replaced with the analogous fragment from these clones. The resulting clones were designated pM18 ($C_8$) and pM19 ($C_{12}$).

The pM16, pM18, and pM19 transcripts all proved to be infectious in mice. Transfection of HeLa monolayers with RNA transcripts from any of the three clones resulted in adequate plaque formation. The specific infectivity of pM16 was about $10^2$ pfu per microgram of transcript RNA This infectivity was lower than that observed for wild-type vRNA, which is $10^5$ pfu per microgram of RNA, but the ability of clone-derived RNA to form plaques was very reproducible.

Our work in Duke et al., *Nature* 343 [6257] 474-476 (February, 1990) (not prior art) describes the intracerebral inoculation of mice with the shortened poly(C) tract Mengovirus, pM16. We have now successfully developed methods to inoculate monkeys and pigs, animals from orders different than mice, with pM16. Inoculation of these animals demonstrates that the pM16-containing vaccine can protect animals in other mammalian Orders.

The general protocol of the primate experiments is as follows: monkeys were inoculated either intramuscularly, intracerebrally, or orally with pM16 virus. Fecal and blood samples were taken from the animals at routine intervals and screened for the presence of virus in the blood and feces (to show infection) and virus-neutralizing antibodies in the blood.

The presence of virus in blood or fecal samples was assessed by standard plaque assay on HeLa monolayers or BHK cells as in Pallansch and Rueckert, *Methods in Enzymology* 78: 315-325 (1981). After inoculation with pM16, animals were found to have live virus in their feces and blood. Nevertheless, these animals did not develop fatal disease symptoms.

Microneutralization plaque reduction assays were performed on the primate blood serum to evaluate the titre of antiviral antibodies. FIGS. 2-4 contain the results of these assays. Data are presented as the minimum effective dilution of serum to confer complete protection to a HeLa monolayer from $10^4$ pfu of infectious wild-type Mengovirus. Assays were always carried out in duplicate and the results averaged for a final titre. An analogous protocal for the assay is found in Sherry and Rueckert, *J. Virology*, 53: 137–143 (1985) and Duke, et al. *Nature* 343: 474–476 (1990).

FIG. 2 represents data collected in an experiment designed to compare intramuscular and oral routes of inoculation of primates. Animals were inoculated with $10^8$ pfu of pM16. Both routes of inoculation proved to be successful. Neither category of animal developed symptoms, and both categories developed a serum antibody titre.

The experiment reflected in FIG. 3 examines the viral dose effect in intramuscular inoculation. FIG. 3 indicates that all doses between $10^3$ through $10^7$ pfu produced an antibody titre by the ninth day post-injection.

FIG. 4 reports the result of intracerebral inoculation of $2 \times 10^8$ pfu of pM16 virus. Animals did not have any signs of illness after inoculation, and, with one exception, there were no fatalities. Necropsy reports of the one dead animal were inconclusive as to the cause of death, but animal caretakers believed it died from injuries sustained in a fight with cage mates, rather than experimental procedures.

Experiments designed to test the short poly(C) tract vaccine in Artiodactyls are described in FIG. 5. Six *Sus scrofia* were chosen for the experiment. Four of the animals (numbers 1 through 4) received intramuscular inoculations containing $10^6$ pfu of PM16 virus. The other two animals (number 5 and 6) received equivalent inoculations containing only a buffer sample. Blood samples were collected and titered for antibody as described above. Animal number 4, which showed no antibody titre at day 28, was reinoculated. The reported titre at 42 days is actually the titre obtained two weeks after the second inoculation. As FIG. 5 indicates, all of the non-control pigs seroconverted. None of the animals exhibited disease symptoms.

28 days after inoculation, animals 1, 2 and 5 were challenged with intramuscular inoculation of wild-type EMCV virus at a concentration of $10^4$ pfu. Animals 1 and 2 resisted the challenge and did not show symptoms of the disease. Animal 5 developed disease symptoms which lasted 7 to 10 days before the animal recovered.

We believe that poly(C)-mediated attenuation first becomes evident when the tracts are shortened to less than 40 nucleotides (for example, $C_{26}UC_{10}$). A higher degree of attenuation, measured by increased amount of virus required to kill the animal, can be achieved when the tracts are further shortened to lengths of less then thirty nucleotides (for example $C_{13}UC_{10}$). Beyond thirty nucleotides the removal of additional bases does not provide significantly greater attenuation but may reduce the potential for sequence reversion in these strains.

The method of the present invention helps protect non-murine animals against picornavirus-caused disease. As demonstrated by the examples above, a short tract picornavirus vaccine may be used to protect mammals such as pigs and monkeys against picornavirus disease. The scope of the present invention specifically includes the use of short tract picornaviruses other than pM16 to immunize non-murine animals against picornaviral disease. pM16 is merely an example of a short poly(C) tract picornavirus.

Other picornaviruses besides Mengovirus, such as EMCV, could be used to create short tract progeny by a method analogous to that disclosed in Duke and Palmenberg (supra.) Viral RNA (vRNA) may be isolated by methods analogous to those of Rueckert and Pallansch, *Methods of Enzymology* 78: 315–325 (1981). This vRNA may be used as a template for cDNA synthesis, as in Duke and Palmenberg (supra.). As we have demonstrated, cDNA synthesis through the poly(C) tract will result in artificially shortened poly(C) tracts. By the terms "shortened tract" or "short tract", we mean a poly(C) tract that is shortened relative to the poly(C) tract found in the wild-type virus. Thus, a 5'-non-coding region that has had the poly(C) tract completely removed would still have a "shortened poly(C) tract" as that term is used in the claims.

The method of the present invention should also be successful with picornavirus vaccines containing a picornavirus with sequence alterations or deletions in regions outside the poly(C) tract. It is, of course, necessary for the virus to be capable of replication and that the live virus be capable of eliciting antiviral antibody production.

By the term "effective amount" of vaccine, we mean an amount of virus that will elicit antiviral antibody formation and inhibit viral disease. The examples above disclose a dose that is effective in eliciting antiviral antibody formation in the blood serum of primates and Artiodactyls.

We also specifically envision that inoculation with any short tract cardiovirus will protect an animal against disease caused by any other poly(C) tract-containing cardiovirus, and that inoculation of an animal with a short tract aphthovirus will protect an animal against disease caused by any other poly(C) tract-containing aphthovirus. By the term "immunize", we mean any lessening or inhibition of viral disease. By the term "recombinant" we mean a virus that is a progeny of a viral gene that has had its gene sequence modified by artificial (non-natural) means.

We claim:

1. A method of inhibiting disease caused by a cardiovirus in a live, non-murine mammal, where the disease is caused by a cardiovirus having a non-coding poly(C) tract of at least fifty nucleotides, a method comprising:

administering to the non-murine mammal an effective amount of a vaccine which contains a live, recombinant cardiovirus that has a shortened poly(C) nucleotide tract, antibodies against the disease-causing cardiovirus are formed in vivo in the mammal and the disease is thereby inhibited;

wherein the non-murine mammal is an animal selected from the group consisting of primates and swine and wherein the non-murine mammal is a host for said disease causing cardiovirus.

2. The method of claim 1, wherein the cardiovirus contained in the vaccine is a Mengovirus with a shortened poly(C) nucleotide tract.

3. The method of claim 1, wherein the shortened poly(C) tract has less than 40 nucleotides.

4. The method of claim 1, wherein the shortened poly(C) tract has less than 24 nucleotides.

5. The method of claim 1, wherein the vaccine is administered orally.

6. The method of claim 1, wherein the vaccine is administered intramuscularly.

7. The method of claim 1, wherein the vaccine is administered intraperitoneally.

8. The method of claim 1, wherein the vaccine is administered intracranially.

9. The method of claim 1, wherein the mammal is an animal selected from the group consisting of non-human primates and swine.

* * * * *

UNITED STATES PATENT AND TRADEMARK OFFICE
CERTIFICATE OF CORRECTION

PATENT NO. : 5,229,111

DATED : July 20, 1993

INVENTOR(S) : Ann C. Palmenberg, et al.

It is certified that error appears in the above-identified patent and that said Letters Patent is hereby corrected as shown below:

| | |
|---|---|
| Column 1, line 40 | tractcontaining s/b tract-containing |
| Column 2, line 44 | in vivo s/b in vivo |
| Column 6, line 15 | replication s/b replication, |
| Column 6, line 44 | in vivo s/b in vivo |

Signed and Sealed this

Twelfth Day of April, 1994

*Attest:*

BRUCE LEHMAN

*Commissioner of Patents and Trademarks*

*Attesting Officer*